US012638322B2

(12) United States Patent　　　　　(10) Patent No.:　US 12,638,322 B2

Kips et al.　　　　　　　　　　　　　(45) Date of Patent:　　May 26, 2026

(54) MACHINE FOR DISPENSING A CONTROLLED AMOUNT OF A COSMETIC COMPOSITION

(71) Applicant: L'OREAL, Paris (FR)

(72) Inventors: Robin Kips, Clichy (FR); Vincent Marchal, Aulnay-sous-Bois (FR); Thibault Chauffier, Clichy (FR); Jean-Christophe Bichon, Clichy (FR); Loïc Cardon, Clichy (FR); Claire Crochet, Saint-Ouen (FR)

(73) Assignee: L'Oreal, Paris (FR)

( * ) Notice: Subject to any disclaimer, the term of this patent is extended or adjusted under 35 U.S.C. 154(b) by 720 days.

(21) Appl. No.: 17/904,927

(22) PCT Filed: Jan. 12, 2021

(86) PCT No.: PCT/EP2021/050453

§ 371 (c)(1),
(2) Date: Aug. 24, 2022

(87) PCT Pub. No.: WO2021/170302

PCT Pub. Date: Sep. 2, 2021

(65) Prior Publication Data

US 2023/0127741 A1　　Apr. 27, 2023

(30) Foreign Application Priority Data

Feb. 27, 2020　　(FR) ........................................ 2001971

(51) Int. Cl.
G01F 11/02　　　(2006.01)
A45D 44/00　　　(2006.01)
(Continued)

(52) U.S. Cl.
CPC ............ G01F 11/029 (2013.01); A45D 44/00 (2013.01); G01G 13/285 (2013.01);
(Continued)

(58) Field of Classification Search
CPC . G01F 11/029; A45D 44/00; A45D 2200/058; G01G 13/285; G01G 19/414;
(Continued)

(56)　　　　　　　References Cited

U.S. PATENT DOCUMENTS

| | | |
|---|---|---|
| 4,976,377 A | 12/1990 | Higuchi et al. |
| 5,163,010 A | 11/1992 | Klein et al. |

(Continued)

FOREIGN PATENT DOCUMENTS

| | | |
|---|---|---|
| EP | 0 304 093 A2 | 2/1989 |
| EP | 0 443 741 A1 | 8/1991 |

(Continued)

OTHER PUBLICATIONS

International Search Report issued on Apr. 4, 2021 in PCT/EP2021/050453 filed on Jan. 12, 2021, 4 pages.

(Continued)

*Primary Examiner* — Michael Collins
(74) *Attorney, Agent, or Firm* — Christensen O'Connor Johnson Kindness PLLC

(57)　　　　　　　　ABSTRACT

The present application relates to a device for dispensing a determined weight of a cosmetic product into a receptacle from a reservoir, the device comprising at least one electro-mechanical member capable of moving an amount of cosmetic product from said reservoir installed in the device to a dispensing zone of said device where said amount of product may be transferred through a nozzle into the interior of the receptacle received in said dispensing zone, the device comprising a controller configured to deliver a control signal to the electromechanical member according to an error with respect to a setpoint corresponding to the determined weight of cosmetic product to be delivered, said error being determined on the basis of a weighing datum obtained by at least one weighing cell for the reservoir installed in the receiving (Continued)

zone, the device being characterized in that the controller is a reinforcement-learning controller.

16 Claims, 3 Drawing Sheets

(51) Int. Cl.

| | | |
|---|---|---|
| *G01G 13/285* | (2006.01) | |
| *G01G 19/414* | (2006.01) | |
| *G01G 19/417* | (2006.01) | |
| *G06F 18/21* | (2023.01) | |
| *G06N 3/02* | (2006.01) | |

(52) U.S. Cl.
CPC ......... *G01G 19/414* (2013.01); *G01G 19/417* (2013.01); *A45D 2200/058* (2013.01); *A61K 2800/87* (2013.01); *G06F 18/217* (2023.01); *G06N 3/02* (2013.01)

(58) Field of Classification Search
CPC .. G01G 19/417; G01G 17/06; A61K 2800/87; G06F 18/217; G06N 3/02
See application file for complete search history.

(56) References Cited

U.S. PATENT DOCUMENTS

| | | | | |
|---|---|---|---|---|
| 5,478,238 | A | 12/1995 | Gourtou et al. | |
| 9,519,927 | B1 | 12/2016 | Tuan et al. | |
| 10,239,079 | B2 * | 3/2019 | Ränsch | A45D 34/00 |
| 11,911,733 | B2 * | 2/2024 | Jang | A45D 34/00 |
| 12,083,487 | B2 * | 9/2024 | Jang | A45D 34/04 |
| 12,127,664 | B2 * | 10/2024 | Pack | G06Q 10/08 |
| 2005/0092772 | A1 | 5/2005 | Miller et al. | |
| 2009/0090431 | A1 * | 4/2009 | Yacko | G01F 11/029 |
| | | | | 141/192 |
| 2009/0218007 | A1 | 9/2009 | Saranow et al. | |
| 2013/0037043 | A1 * | 2/2013 | Samain | G16H 50/20 |
| | | | | 222/129 |
| 2015/0089751 | A1 | 4/2015 | Landa et al. | |
| 2016/0279329 | A1 * | 9/2016 | Faisal | A61M 5/1723 |
| 2017/0151538 | A1 | 6/2017 | Balooch et al. | |
| 2017/0208920 | A1 | 7/2017 | Thiebaut et al. | |
| 2021/0298442 | A1 * | 9/2021 | Jang | A45D 34/00 |
| 2022/0250105 | A1 * | 8/2022 | Baumann | B05B 11/00442 |

FOREIGN PATENT DOCUMENTS

| | | | |
|---|---|---|---|
| EP | 1093842 | A1 | 4/2001 |
| FR | 3 087 428 | A1 | 4/2020 |
| WO | WO 91/18327 | A1 | 11/1991 |
| WO | 2008046518 | A1 | 4/2008 |
| WO | WO 2015/067956 | A1 | 5/2015 |
| WO | 2017213834 | A1 | 12/2017 |
| WO | 2019161360 | A1 | 8/2019 |
| WO | 2019180252 | A | 9/2019 |

OTHER PUBLICATIONS

Mnih, V., et al., "Playing Atari with Deep Reinforcement Learning," Dec. 2013, pp. 1-9. doi.org/10.48550/arXiv.1312.5602.
Sutton, R.S., and Barto, A.G., "Reinforcement Learning: An Introduction," 2 ed., The MIT Press, Cambridge, Mass. © 2014, 2015, 352 pages.
Culliney, K., "Beyond just the counter': L'Oréal to launch digital Lancôme Shade Finder for Le Teint Particulier" (Nov. 2020) (available at https://www.cosmeticsdesign-europe.com/Article/2020/11/25/L-Oreal-to-launch-digital-Lancome-Shade-Finder-for-Le-Teint-Particulier/), 5 pages.

* cited by examiner

[Fig. 1]
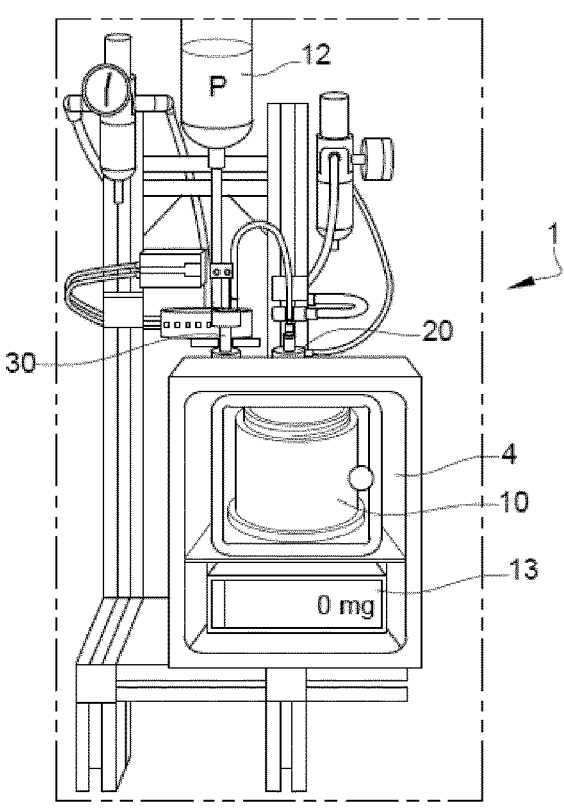
[Fig. 2]
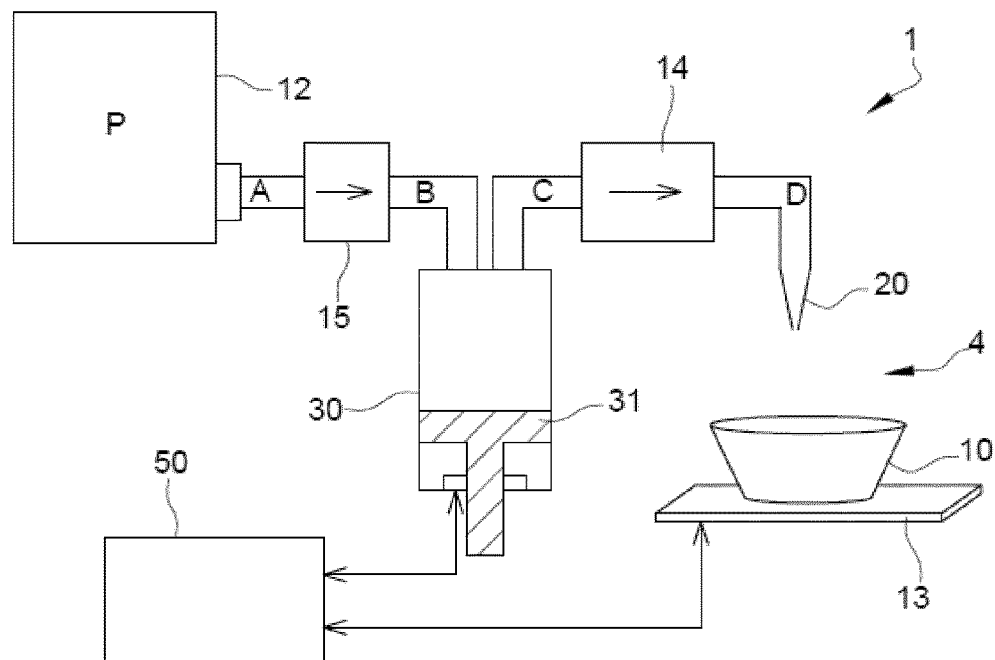

[Fig. 3]
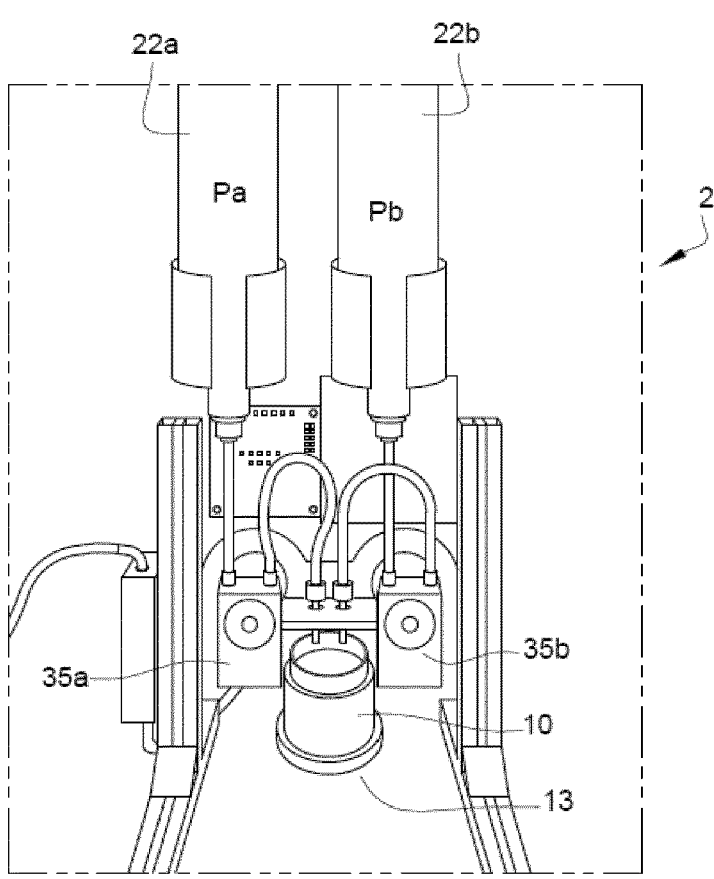
[Fig. 4]
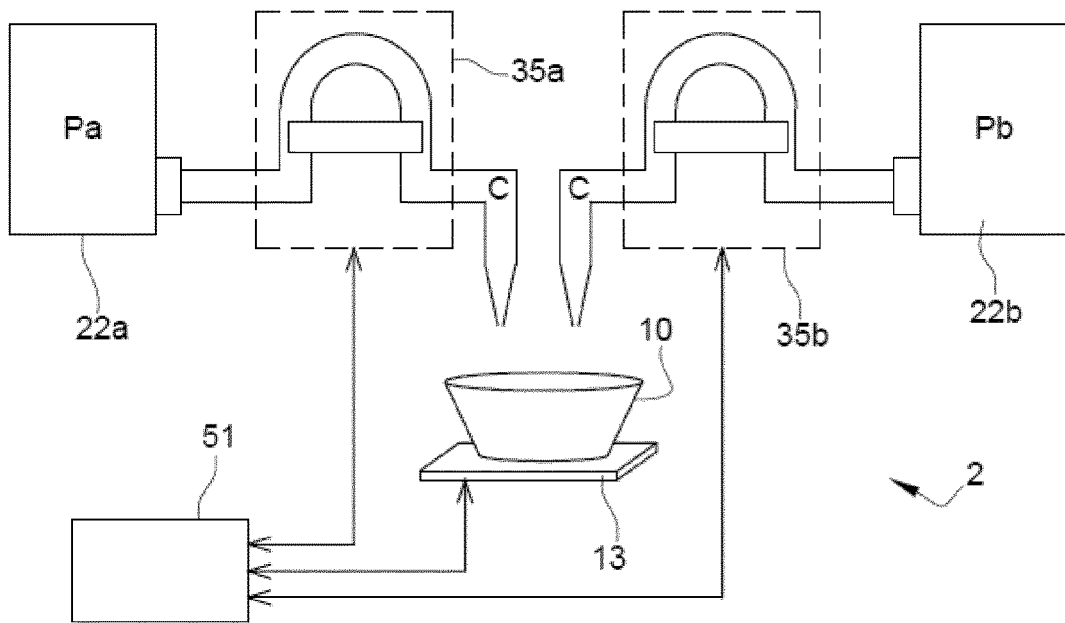

[Fig. 5]
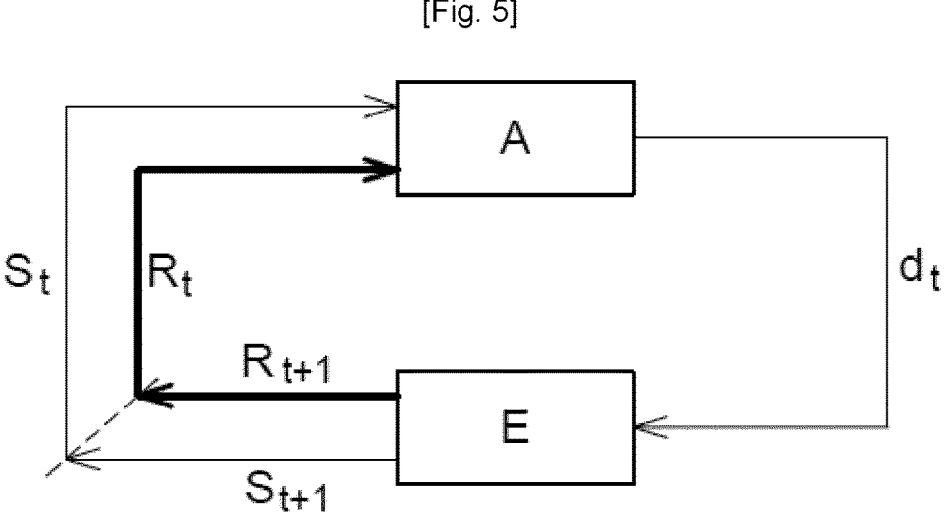
[Fig. 6]
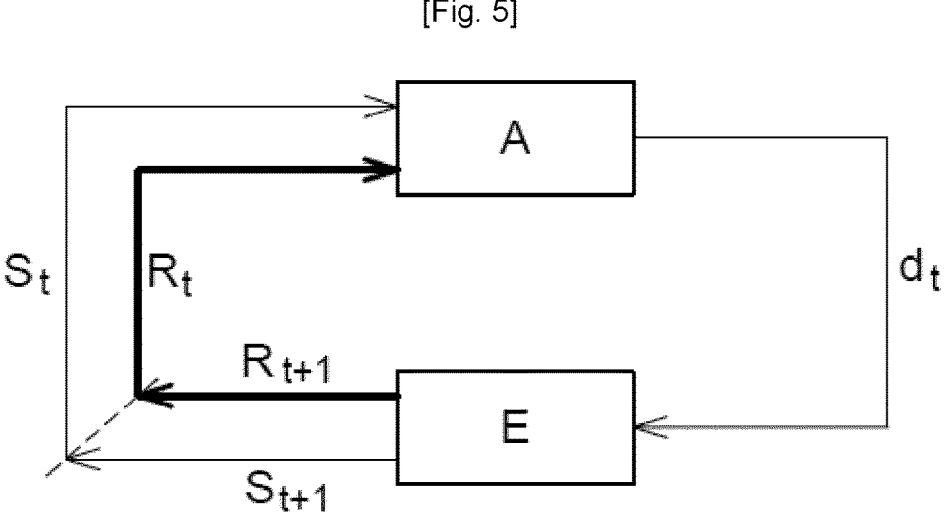

MACHINE FOR DISPENSING A CONTROLLED AMOUNT OF A COSMETIC COMPOSITION

The present invention relates to a machine for the controlled dispensing of a determined amount of at least one cosmetic product into a receptacle from a reservoir, the machine comprising a dispensing zone configured to receive the receptacle capable of containing said amount of cosmetic product to be dispensed.

A "cosmetic product" is understood to be any product as defined in Regulation (EC) No 1223/2009 of the European Parliament and of the Council of Nov. 30, 2009 on cosmetic products. Thus, a cosmetic product is generally defined as being a substance or a mixture intended to be brought into contact with superficial parts of the human body (epidermis, body-hair and head-hair systems, nails, lips, and external genitalia) or with the teeth and the oral mucous membranes in order, exclusively or mainly, to cleanse them, fragrance them, modify their appearance, protect them, keep them in good condition, or correct body odours.

The cosmetics industry always aims to improve consumer experience and to offer products and compositions that are ever more adapted to consumers' needs and their specific characteristics. This trend is generally termed "customization".

It is thus, for example, known practice to recommend foundations on the basis of one or more characteristics of a user's skin (see, for example, documents U.S. Pat. Nos. 5,478,238 and 9,519,927). The treatment or cosmetic product designed in accordance with the user's specific characteristics may be a ready-formulated finished product selected from a catalogue or database, or a customized product of which the composition itself has been determined on the basis of the individual characteristics obtained (for example, "Le Teint Particulier"® offered by LANCÔME®).

It is also known practice to offer customized hair products of which the composition is determined on the basis of different properties of the user's hair (for example US20150089751).

The product may then be purchased in the conventional way or ordered by the individual in question. In the case of a "custom-made" product, said product may be manufactured directly at the point of sale (store or salon, for example) using a device capable of dispensing components in accordance with the custom-made composition determined beforehand.

Such devices are, for example, described in documents US2017151538A1 in the case of a foundation and EP0443741, US20150089751, cited above, in the case of hair-colouring products.

In general, such machines comprise a body configured such as to receive a plurality of cartridges of different cosmetic products made from ingredients suitable for being combined in order to form a final cosmetic composition. The machine may thus comprise one or more cartridges of one or more cosmetic bases (taking, for example, the form of a cream) and/or one or more cartridges of active cosmetic products (dyes, pigments, active care products, etc.) intended to be added to one of the cosmetic bases in order to form the final composition in accordance with the consumer's wishes.

The machines also comprise a dispensing zone configured to receive a receptacle capable of containing said cosmetic composition. In the case of products of care-cream or foundation type, the receptacle may conventionally be a bottle or jar. In the case of a hair-colouring product, the receptacle may, in particular, be a mixing bowl (see for example documents EP1093842A1, US20050092772 and US20090218007A1).

Electromechanical systems of pump or piston type take up an amount of cosmetic product and move it from the desired reservoir or cartridge to the dispensing zone where the product may be transferred into the receptacle via a dispensing nozzle arranged, or capable of being arranged, opposite an opening of said receptacle. Among the dispensing systems used, peristaltic pumps, piston systems, and syringe systems (intake/delivery) may be mentioned. Document WO2019161360A1 thus describes several conventionally used dispensing systems.

In the case of a custom-made cosmetic product of which the composition is defined to suit the user and is manufactured on demand, either in-store or in the user's home, it is important to be able to precisely control the weight of each ingredient dispensed into the receptacle, even if the machine is equipped with electromechanical systems with controlled movement of metering-pump or metering-piston type.

Specifically, one difficulty is that independently of the degree of precision of the dispensing member, the amount of product taken up and moved by the dispensing system generally corresponds to a given volume of product and not directly to its weight. Thus, in the case of a metering piston, for example, it is the movement of the piston that defines the volume of product dispensed. The amount of product in terms of weight therefore depends on the density of said product. The same applies for pumping systems, in which the viscosity of the product also plays a role.

Such dispensing members therefore have to be calibrated with respect to the product that it is required to deliver and to the components used (diameter of pipes, sealtightness of the system, nozzles, etc.) in order to determine the weight of product dispensed according to an operating parameter of the dispensing system such as the duration of operation of the pump (potentially in association with a flow regulator, see, for example, WO2008046518A1), the movement of the piston or the number of revolutions of a piston mounted on a threaded stem (see US2017208920A1) or of a peristaltic pump (see WO2017213834).

In order to provide better control of the amounts of products dispensed, one common solution is to equip the receiving zone with a weight sensor (load cell) as described in several documents cited above. This weight sensor may in particular take the form of scales comprising a pan on which the receptacle is placed in the dispensing zone. The weight datum returned by the sensor is used by a controller to regulate and control the dispensing member.

One known regulation and control method is thus to control the dispensing system step by step, or revolution by revolution, and to check whether or not the target weight has been reached with each step of the system. Of course, such a control method greatly increases the time required to dispense the desired amount. Additionally, the degree of precision of the system depends on the amplitude of the control step and the unitary movement defined. The smaller the control step, the more precise the system can be, but the duration required to dispense the desired weight of product will be accordingly longer.

A second common regulation and control method is using a PID-type controller allowing, for example, continuous dispensing of the product with faster initial product dispensing followed by slowing of the dispensing member nearing the target weight until arriving as close as possible to this target. This type of controller is fully understood and is widely used in all areas of industry, including in the rearing of livestock for the controlled dispensing of feed. This type of PID controller is particularly suitable for the control of linear systems and is generally suited for such dispensing systems of which the rules of operation may be known a priori.

One alternative to a PID controller could be a fuzzy logic controller, or FLC. However, implementing such a controller requires relatively high computing power and is extremely complex to adjust. Furthermore, fuzzy logic is generally recommended for addressing, more particularly, the problem of obtaining vague and imprecise information on the state of the system. This is not the case with a cosmetic dispensing machine equipped with a weighing cell, since it would be difficult to qualify the data returned by this weighing cell as vague and imprecise. Such a system would therefore not particularly be considered for controlling a simple system such as a machine for dispensing a cosmetic product of which the control rules are easily determinable or known a priori.

Thus, although potentially complex to optimize, a PID controller might be preferable, and all the more so with the availability of methods facilitating the adjustment thereof using, for example, genetic algorithms.

However, it has been observed that this type of common control and regulation has limits and might be insufficient to achieve optimal control and regulation of the dispensing of a cosmetic product into a receptacle by a driven electromechanical member. Thus, there is a need for a machine for dispensing a cosmetic product of which the dispensing system is easily adaptable and which has a reduced need for maintenance, calibration and adjustment.

The present application aims to address these limitations and to that end proposes a device for dispensing a determined weight of a cosmetic product into a receptacle from a reservoir, the device comprising at least one electromechanical member capable of moving an amount of cosmetic product from said reservoir installed in the device to a dispensing zone of said device where said amount of product may be transferred through a nozzle into the interior of the receptacle received in said dispensing zone, the device comprising a controller configured to deliver a control signal to the electromechanical member according to an error with respect to a setpoint corresponding to the weight of cosmetic product to be delivered and determined on the basis of a weighing datum obtained by at least one weighing cell for the reservoir installed in the receiving zone, the device being characterized in that the controller is a reinforcement-learning controller.

Thus, by implementing a reinforcement-learning controller, it is possible to obtain a dispensing device that is extremely adaptable with respect to its external environment and its change.

More precisely, the reinforcement-learning controller implements a strategy (policy function) that defines an action to be performed by the electromechanical member according to a state of the device during an operation of dispensing a cosmetic product. The strategy is adapted so as to optimize a quantitative reward over time.

Given the precision required and the fact that it is not desirable to exceed the target amount of product to be dispensed, it might be useful to chose a "prudent"-type strategy. The reward function will be directly dependent on the error, i.e. the difference between the target amount to be dispensed and the amount actually dispensed as determined from the state of the device. Of course, other methods for accounting for the error and in particular of its history over the course of dispensing (use of a value function) are possible.

The state of the device is defined by the weighing datum representing the weight of cosmetic product dispensed into the receptacle and the difference or error with respect to the target weight of product to be dispensed.

The state of the device may be defined more precisely using other environmental sensors (for example, temperature sensor, hygrometer, etc.). Preferably however, only the weighing datum is used to represent the state of the device with respect to the setpoint weight to be dispensed.

The action to be performed consists of a control signal destined for the electromechanical member and is chosen from among a set of available actions for directly driving the electromechanical member. The action may be a unitary action or correspond to a control profile.

More precisely, the actions consist in moving an actuator of the electromechanical dispensing member by means of numerical control commands. Depending on the type of dispensing member, the available actions could, for example, be of the type: rotate by N steps; move a piston for x seconds at a speed v, move the piston by a distance d, stop control command, etc.

These available actions may be combined to form high-level control commands. These high-level control commands may themselves define a control profile and/or a unitary action for a complex system combining additional members with the electromechanical dispensing member such as supply or shut-off valves that have to be controlled in conjunction with the actuator.

The state of the device may be obtained during the dispensing operation (for continuous reinforcement) and/or at the end of a dispensing operation (for overall reinforcement of an overall action corresponding to a dispensing profile). The state of the device may be obtained during the dispensing operation continuously or discontinuously, preferably at regular intervals, in particular after each unitary action performed.

Specifically, while such a system for dispensing cosmetic products could be considered to be a simple linear system, it has been observed that there are many causes for variability, not only in the environment but also in the dispensing itself.

As explained above, in the case of variation of the physico-chemical characteristics of the product, for example due to the conditions of the environment in which the machine is used or ageing of the product over time, the initial calibration of the dispensing members will no longer be valid, which may lead to errors in dispensing. Thus, if the dispensing member has been calibrated to deliver a given amount of product under normal temperature and pressure conditions (for example, 25° at 1 atm, normal humidity), use of the machine in a very humid environment at 40° and at altitude might require a new calibration procedure there.

The manufacturing tolerances of the various parts of the system and their wear over time may also be a variation factor. This is why each machine should ideally be calibrated individually.

Furthermore, if a product is replaced with a different product exhibiting different physico-chemical characteristics for which the machine has not been calibrated, it will likewise be necessary to calibrate the dispensing member. Thus, a cartridge of a product that is brand new and, for example, much more viscous than the initial product will not be able to be dispensed precisely directly by the machine without a specific intervention. The system is not "plug and play".

Although these variations will have only a small or easily correctable effect for large amounts or for a product manufactured under known conditions, the relatively small amount of product to be delivered for an "on-demand" product makes such metering errors particularly sensitive.

In the particular case of hair colouring where variation in the amount of dye may have a substantial effect on the ultimate colour obtained, it is especially important to implement reliable and precise dispensing systems.

Although control by reinforcement learning is already known and used in various sectors, it is generally aimed at controlling complex systems of which the rules governing the environment are not known or highly uncertain. This is why this type of controller is commonly used in aeronautical or automotive applications for controlling drones and self-driving vehicles, for example.

Thus, control by reinforcement learning is applied successfully in fields as diverse as autonomous helicopter flight, the movement of robots equipped with "legs" that they have to "learn" to control, routing in cellular telephone networks, control of factories or the indexing of web pages by a search engine.

More particularly, document WO2015067956A1 is known which describes the use of a controller by reinforcement learning for dispensing an anaesthetic product to a patient. The choice of such control is motivated by the fact that the state of the patient is difficult to determine and to predict by means of equations using their vital signs ("patient-specific policy", determining rules of administration specific to the patient).

In the present field of application, it has been observed that despite a priori simple rules of operation of the system and a weighing datum that can be obtained precisely and reliably, there are actually many causes for variability in the system, in particular due to the products to be dispensed themselves or to parts of the machine itself and not entirely to an unpredictable or difficult-to-measure external environment.

Thus, in contrast to document WO2015067956A1 cited above which envisages a learning module that aims to determine a "policy function" specific to the patient to whom the product is dispensed, the present application envisages a learning module that aims to determine a "policy function" specific to the machine and to the products dispensed.

The position of the applicant is thus that the known prior cases of use of such a learning module, including in a machine for dispensing a product, in no way prompt the use of this type of module for a dispensing machine in which the variability actually comes from the machine itself (components or products to be dispensed).

Furthermore, it is apparent from document WO2015067956A1 that the action that has to be selected by the learning module is an action that determines the amount of product to be administered to the patient (Claim 1). It is therefore a matter of using the reinforcement-learning module to determine and adapt a target (setpoint) amount for dispensing and not, as in the present application, of checking that the amount dispensed is in accordance with the target amount and, where appropriate, adapting the dispensing profile (all of the driving actions for the electromechanical member) in order to correct for variations. Document WO2019180252A1 is similar in so far as the reinforcement-learning module is used to determine the size of coffee cups introduced into the machine and to deduce the amount of coffee to be used therefrom. In the present application, the amount of product to be dispensed is determined (fixed, by the recipe for the composition, etc.) and the reinforcement-learning module is implemented to control that the dispensing members (pumps, tubes, cosmetic product in the reservoir) allow the desired amount to be dispensed and, where appropriate, adapt the dispensing profile. It is therefore essentially a matter of adapting to an internal variability of the dispensing machine rather than directly to an external variability.

The implementation of a control unit using a reinforcement-learning module that adapts the control profile of the electromechanical member rather than the setpoint that sets the amount of product affords, in particular, the following advantages:

adaptability to a cosmetic product exhibiting different physico-chemical characteristics from the product used previously in the dispensing machine, without a need for prior calibration or recalibration, reliable and robust dispensing capable of adapting to variations in the environment such as temperature, humidity and pressure, and their effect on the cosmetic product to be dispensed, in particular its density, without a need for recalibration, reliable and robust dispensing with respect to manufacturing variations and tolerances in the dispensing machine, without a need for recalibration, reliable and robust dispensing with respect to the replacement of elements of the machine in maintenance operations, relative independence with respect to the dispensing technology employed.

For more precise explanations of the principles of operation and the concepts relating to reinforcement learning, reference may be made to the article "*Playing Atari with Deep Reinforcement Learning*", which describes the implementation of such a system, and to "*Reinforcement Learning: An Introduction*" by Richard S. Sutton and Andrew G. Barto.

According to a first variant embodiment, the reinforcement-learning controller uses a regression algorithm according to a Gaussian process.

In the case of the Gaussian process, a prior calibration phase is required. In the calibration phase, the controller and its learning model will explore various control actions for the electromechanical member, or even all of the available actions, and observe the corresponding amounts delivered (associated obtained state). In this calibration phase, the amount dispensed is not controlled, and the product is subsequently discarded.

The use of Gaussian process regression makes it possible in particular to obtain an estimate of the confidence of the system in its performance according to the target amount. This confidence may be integrated into the strategy. Thus, in a calibration phase, the system may explore the various strategies for the various amounts so as to minimize the risk of error for all of the amounts.

According to a second variant, the reinforcement-learning controller uses a deep-reinforcement-learning algorithm.

In the case of deep reinforcement learning, it is possible to train the model to calibrate itself dynamically while performing the task of dispensing. For example, the strategy adopted could initially be of "prudent" type with behaviour close to "step by step", or revolution by revolution, and as the learning module becomes more confident in its ability to dispense precisely, the strategy could be adapted accordingly.

According to a first embodiment, the reinforcement-learning controller is based on an initial predictive model. Such a build allows faster adaptation of the controller to changes in its environment.

Alternatively, the reinforcement-learning controller operates without an initial predictive model. Such a build allows greater versatility with respect to potential changes to the environment and especially to the components of the machine. Thus, even if, for example, the electromechanical dispensing member had to be replaced with a member using different technology, the adaptation of the controller in order to reach a good degree of dispensing precision would be possible (this is also possible with an initial predictive model but with less adaptability).

In the case of adaptation according to Gaussian process regression, a calibration phase such as mentioned above will be required after modifying a component of the machine. However, in the case of adaptation of deep-learning type, such a calibration phase is not strictly necessary.

According to a first option, the reinforcement-learning controller has been pre-trained prior to commercial use of the device. Such pre-training allows the device to be immediately operable at its site of sale and also allows faster adaptation to local environmental conditions. Of course, the device may be trained again at its location of commercial use in order to adapt the controller more finely to the particularities of its environment of use.

According to a second option, the reinforcement-learning controller has not been pre-trained prior to commercial use of the device.

According to a first embodiment, the reinforcement-learning controller is configured to perform an adaptation of control strategy following a plurality of dispensing operations, in particular after a determined number of dispensing operations and/or after a given period of time, on the basis of the operations performed during this period of time, together defining a dispensing profile. In particular, the controller may thus update its control strategy by using all of a day's dispensing operations.

Alternatively or additionally depending on the type of learning implemented by the controller, this controller is configured to perform one or more adaptations of control strategy over a dispensing operation, in particular at regular intervals after a unitary control action (or high-level action defining a unitary action for a complex electromechanical dispensing member). Thus, the learning of the dispensing model by the controller may be performed "on the fly" or live, with adaptation of the model in real time. This type of operation is particularly suited to machines in which a product to be dispensed may be replaced with a product with different physico-chemical characteristics in order to allow adaptation over the course of the dispensing itself. This limits the risk of erroneous or imprecise dispensing before adaptation of the model on the basis of a plurality of previous complete dispensing operations.

Preferably, the electromechanical dispensing member is a positive-displacement pump, for example a peristaltic pump.

Alternatively, the electromechanical dispensing member is a syringe dispensing by intake followed by delivery. The electromechanical dispensing member may also be a piston.

Advantageously, the device is configured to receive a plurality of reservoirs that are configured for functionally different cosmetic ingredients, said functionally different cosmetic ingredients being capable of being combined so as to form a cosmetic product. Each assembly formed of a reservoir of a cosmetic ingredient and of an associated electromechanical dispensing member has an associated controller and dispensing model. Even though, physically, the controller may be common, functionally, each dispensing module has its own learning model.

The present invention also relates to a method for controlling an electromechanical dispensing member with which a device according to the invention is equipped, characterized in that it comprises the steps for:

providing a setpoint representing a determined weight of product to be dispensed, sending a control signal to the electromechanical member, obtaining, from the weighing cell, the weight of product dispensed following the execution of the control command by the electromechanical dispensing member, determining a difference between the weight of product dispensed following the execution of the control command and the setpoint, modifying the control signal by means of a reinforcement-learning process with a view to minimizing the difference.

According to a first embodiment, the control signal corresponds to a complete dispensing profile of the setpoint and is modified after at least one complete dispensing operation, preferably after a plurality of complete dispensing operations, in particular after a predetermined number of operations and/or after a determined time interval.

According to a second embodiment, the control signal corresponds to a unitary incomplete dispensing action, the control signal being modified at least once over the complete dispensing process, the steps of sending the control signal to the electromechanical dispensing member, of obtaining and of determining the difference in dispensing and of adapting the control signal being repeated for as long as said obtained difference is greater than zero and, preferably, greater than a minimum amount that can be dispensed by the electromechanical member.

The invention may be understood better on reading the following description, accompanied by non-limiting implementation examples thereof, with reference to the appended drawings, in which:

FIG. 1 is a photograph of a dispensing machine according to the invention implementing an electromechanical dispensing member of motorized-piston-syringe type for dispensing an amount of cosmetic product contained in a main reservoir.

FIG. 2 is a functional schematic depiction of the machine of FIG. 1.

FIG. 3 is a depiction of another embodiment of a dispensing machine according to the present application implementing electromechanical dispensing members of peristaltic-pump type for dispensing, in determined amounts, two different cosmetic products each contained in an associated main reservoir.

FIG. 4 is a functional schematic depiction of the machine of FIG. 3.

FIG. 5 is a reinforcement learning diagram.

Fig. 6 is a set of graphs showing adaptation of a control strategy according to a simulation function.

It is important to note that although illustrated for the sake of clarity by means of machines using only a small number of reservoirs (a single main reservoir for the system of FIG. 1 and two reservoirs for the system of FIG. 3), the present application is of course not limited to a given, minimum or maximum, number of reservoirs, and targets more generally dispensing machines that comprise a plurality of reservoirs capable of containing together functionally different cosmetic ingredients which may be combined with one another to form an end cosmetic composition. Thus, in the particular case of a machine for preparing a customized hair-colouring composition, one or more main reservoirs could contain one or more base creams to which will be added one or more dyes contained in other reservoirs so as to obtain the desired hair-colouring composition. As mentioned above, and illustrated in FIGS. 1 and 2, the present application may be applied to the dispensing in loose form of a determined amount of a cosmetic product of which a larger amount is contained in the reservoir. The machine may therefore have only one reservoir from which will be dispensed a relatively small amount of the product contained in said reservoir. The present invention is more particularly relevant for non-industrial machines designed to dispense relatively small amounts corresponding substantially to the amounts present in a bottle intended for sale. Thus, the maximum amount of product to be dispensed (setpoint) is preferably smaller than 100 g, preferably smaller than 50 g, or even smaller than ten grams or even smaller than one gram for ingredients featuring as additives to a cosmetic base dispensed in a larger amount.

For further specifications, reference could be made to the documents cited above which describe the make-up of such machines in detail. It is also important to note that the present application is not limited to one particular application, and although illustrated using a machine for producing a customized hair dye, it is applicable to other products such as, for example, a customized foundation or a customized lipstick composition.

Furthermore, although the present application is preferably illustrated using systems for dispensing liquid or cream products, it is applicable to systems for dispensing solid products, in the form of fluid powder, or of beads or tablets.

FIG. 1 is an illustration of a first exemplary embodiment of a machine 1 for dispensing a cosmetic product. FIG. 2 is a functional schematic depiction of the machine of FIG. 1.

The machine 1 comprises a main reservoir 12 that initially contains a substantial amount (capacity for example greater than ½ litre, or even greater than 1 litre) of a cosmetic product P to be dispensed in smaller amounts, typically of the order of a few grams for a cosmetic additive to a few tens of grams for a cosmetic base.

Advantageously, the reservoir 12 takes the form of a removable cartridge that can be replaced, in particular when a cartridge is empty, with a cartridge of the same product or of a different product. Such a removable cartridge may in particular take the form of a cartridge with a rigid body or of a flexible pouch. The removable connection of the reservoirs is not the subject of the present application and a person skilled in the art may use any known solution allowing the reservoirs to be installed removably. Exemplary solutions are described in particular in the documents cited above. Another advantageous example of the removable connection of a pouch of liquid product is described in application FR18/71211, which is yet to be published.

The machine 1 also comprises a dispensing zone 4 intended to receive a receptacle 10, in particular a bottle, a jar or a bowl, into which the cosmetic product contained in the reservoir 12 has to be dispensed, and dispensed in a controlled amount. According to the present application, the receiving zone 4 is equipped with scales 13 comprising a pan on which the receptacle 10 is placed. The scales constitute a weighing cell allowing the weight of the receptacle to be measured, and the variation thereof to be tracked over the course of a dispensing operation. The weighing cell thus makes it possible to determine the weight of an actually dispensed product at any time.

The reservoir 12 is associated with an electromechanical dispensing system capable of taking, from said reservoir 12, a determined amount of cosmetic product and of conveying it to the dispensing zone 4 of the machine 1 where said amount of cosmetic product may be transferred into the interior of the receptacle 10 through a corresponding dispensing nozzle 20.

Such electromechanical systems are not the subject of the present invention and a person skilled in the art is free to choose the appropriate transfer system. According to one variant embodiment, the dispensing system may be common to a plurality of reservoirs. Thus, systems are known in which the reservoirs are borne by a carousel capable of bringing each reservoir to the receiving zone where a common piston allows the desired amount of cosmetic product to be ejected into the receptacle located beneath a nozzle borne by said reservoir. As above, the documents cited above give examples of uptake and dispensing systems. Since the present application targets the control and driving thereof, they will not be described further.

In this case, the machine 1 implements an uptake and dispensing system of piston-syringe type 30 of which the general operation is described in document WO2019161360A1. The syringe 30 comprises a piston 31 of which the movement is controlled by a motor. The syringe 30 is fluidically connected both to the reservoir 12, so as to be able to take up the content thereof, and to the dispensing nozzle 4. A first non-return valve 13 arranged between the reservoir 12 and the syringe 30 and a second non-return valve 14 is arranged between the syringe 30 and the dispensing nozzle 20, thereby ensuring that the cosmetic product flows from the reservoir 12 to the dispensing nozzle 20.

The electromechanical uptake and dispensing system is capable of being controlled and driven by a controller 50 configured to deliver a control signal to the electromechanical member according to the determined weight of product to be dispensed (setpoint) and the weighing datum representative of the amount of said cosmetic product dispensed.

Once the weight of product to be dispensed has been transmitted to the controller for the setpoint, the cosmetic product is dispensed as follows.

After setting the weight of the receptacle (weight dispensed=0) and retracting the piston as far as possible so as to fill the syringe with the cosmetic product to be dispensed, the piston is moved in a controlled manner so as to expel the cosmetic product previously taken up and dispense it into the receptacle through the nozzle.

It should be noted that the inverse is also possible, namely retracting the piston in a controlled manner so as to take up an expected amount of product before pushing the piston all the way so as to dispense all of the amount taken up.

According to the present application, the controller 50 implements a reinforcement-learning algorithm in order to determine the control signal sent to the electromechanical member.

With reference to FIG. 5 and to the definitions commonly used in the field of reinforcement learning, the controller for the electromechanical member implementing the reinforcement-learning algorithm constitutes the "agent" A, while the electromechanical member capable of dispensing the cosmetic product contained in the associated reservoir constitutes the "environment" E on which said agent acts by sending the control signal constituting the "action" $a_t$.

The "state" S of the system corresponds to the difference (or error) between the weight of product dispensed and the determined weight of product to be dispensed (setpoint). The objective of the "agent" A is thus to get as close as possible to zero and defines the "reward" R received in each dispensing step and the "value" over the entire dispensing operation.

The "agent" controller thus acts on the "environment" electromechanical member via the control signal that it sends in response to the "state" of dispensing obtained through the weighing datum.

Unlike a PID-type controller such as described above in which the signal is a given function of the error or difference (the proportional, integral and derivative parameters are set according to the desired dynamics of the system), the use of a reinforcement-learning module allows adaptation and modification of the signal.

In the context of the present application, all or some of the control signals that may be sent to control the electromechanical member constitute all of the actions available to the controller in the context of a dispensing sequence. The actions available to the controller may also be a signal representative of a dispensing profile and of which the parameters may be adjusted (adjustment by reinforcement of PID coefficients for example).

More particularly, in the present case, the dimensional characteristics of the syringe 30 make it possible to establish an a priori correspondence between the movement of the piston 31 and the amount of product dispensed, the distance of movement of the piston from its position of maximum retraction thus constituting a dispensing parameter to be optimized according to the weight to be dispensed.

Such a dispensing model may constitute a predictive model used by the reinforcement-learning algorithm. Alternatively, the reinforcement-learning algorithm may be implemented without a predictive model and construct its own model.

Thus, when the controller receives a setpoint representing a determined weight of cosmetic product to be dispensed, the dispensing model allows the controller to convert the requested weight into an amplitude of movement of the piston 31 and to drive said piston 31 accordingly.

Once dispensing has been carried out, the weight of product actually dispensed is compared with the setpoint and the difference is used to modify the control strategy of the controller for subsequent dispensing operations.

The control strategy may be adapted after each dispensing operation or subsequent to a plurality of dispensing operations, in particular after a determined number of dispensing operations and/or after a given period of time.

In such a case, the reinforcement-learning controller could advantageously use a regression algorithm according to a Gaussian process.

FIG. 6 thus shows the adaptation of the control strategy according to a simulation function sim that represents the weight of product dispensed w as a function of a dispensing parameter d, namely the distance of movement of the piston of the syringe. The points O correspond to "observations", i.e. discrete states of the simulation function provided to the model for learning and reinforcement. The dashed curve and the associated envelope correspond, respectively, to the model estimated m by the controller and to the confidence interval IC associated therewith by the artificial-intelligence module.

It can be seen that for a relatively complex and non-linear simulation function, just nine test dispensing operations are needed to obtain a particularly reliable model.

Experiments have also been carried out in which the dispensing nozzle was changed and in which a dispensing nozzle having a diameter of 0.61 mm was replaced with a dispensing nozzle having a diameter of 1.54 mm. Such a change could occur in the case of maintenance on the machine 1 for which a portion of the dispensing system for which the identical original part is no longer available. It has been observed that a few dispensing operations make it possible to quickly adjust the dispensing model of the controller in order to quickly return to reliable and precise dispensing of the desired amount of product.

Experiments have also been carried out in which the initial cosmetic product was replaced with a cosmetic product exhibiting different physico-chemical characteristics. Similarly, the controller was able to quickly adapt its control strategy to the new dispensing properties of the product.

According to another embodiment, the reinforcement-learning controller uses a deep-reinforcement-learning algorithm allowing adjustment of the dispensing strategy over the course of a dispensing operation, almost in real time.

As above, the learning controller may use a predictive model or be implemented without a predictive model. Thus, the reinforcement-learning controller may perform one or more adaptations of control strategy over a dispensing operation, in particular at regular intervals after a unitary control action. The number of state observations taken into account in the model is thus increased and adapted in real time so as to reach the dispensing setpoint as reliably as possible.

The steps of sending a control signal to the electromechanical dispensing member, of obtaining and of determining the difference in dispensing and of adapting the control signal are repeated for as long as said obtained difference is greater than zero and, preferably, greater than a minimum amount that can be dispensed by the electromechanical member.

In a general and complementary manner, the controller may be pre-trained or not pre-trained prior to commercial use of the device.

FIGS. 3 and 4 show a machine 2 which differs from the machine 1 mainly in that it implements two reservoirs 22a, 22b each containing a different cosmetic product $P_a$, $P_b$ to be dispensed in determined amounts.

The machine 2 also differs in that the dispensing system associated with each reservoir is a peristaltic pump 35a, 35b capable of taking, from the corresponding reservoir, a determined amount of the cosmetic product and of conveying it to the dispensing zone 4 of the machine 2 where said amount of cosmetic product may be transferred into the interior of the receptacle 10 through a corresponding dispensing nozzle 20a.

Unlike the preceding dispensing system of syringe type, where the weight of cosmetic product dispensed depends on the distance of movement of a piston, for a peristaltic pump, the dispensing parameter d could consist of the number of revolutions of a rotor squeezing a tube for conveying the product.

Each peristaltic pump 35a, 35b is capable of being controlled by a controller 51. The controller 51 is common to both pumps 35a, 35b and may drive them sequentially, one after the other. The pumps are driven one after the other due to the presence of a single set of scales beneath the receptacle, since the weight of each product dispensed has to be tracked. Each pump is however driven with its own setpoint for the weight of product to be dispensed and according to a dedicated control process with its own learning by reinforcement.

Where appropriate, it is also possible to envisage having common learning by reinforcement, grouping together all of the dispensing steps for both pumps and products, although this greatly increases driving complexity and the requirements in terms of computer processing capacity.

It should be noted that in general, the weight of cosmetic product to be dispensed serving as a dispensing setpoint for the controller 50, 51 may be determined and transmitted to the controller 50, 51 in multiple ways and is not the subject of the present application.

The weight of product to be dispensed thus determined for each component serves as a dispensing setpoint for the controller for the electromechanical member of the associated reservoir. The data on the weight to be dispensed may be transmitted to the machine and to the controller by any means. In particular, the information may be obtained via an interface implemented on a portable device, such as a touchscreen tablet, and transmitted to the machine wirelessly, in particular by Bluetooth or Wi-Fi, directly or via a remote server.

The amounts or proportions of the various components of the end formulation may be entered manually by the user or an operator from a suitable interface or may be calculated on the basis of the desired end composition.

For example, a user could indicate, via a suitable interface, their desired hair colour. A computer, integrated or not integrated into the machine, could then determine, potentially with the use of additional information specific to the user, a corresponding hair-colouring composition for a hair treatment. The computer will then drive the dispensing of each component.

For a user thus wishing to obtain a cosmetic product P allowing them to obtain a hair colour or a foundation colour C, a computer will determine, for example, that this corresponds to 90% by weight of a colourless or white base cream B, 5% by weight of a first dye A1 and 5% by weight of a second dye A2. From this information, the computer will determine that for an amount of composition of, for example, 30 g, it will be necessary to dispense into the receptacle 27 g of base cream B and 1.5 g of each of the dyes A1 and A2. As mentioned, determining the composition to be delivered is not the subject of the present application and for further examples and details regarding this, reference may be made to the documents cited above and in particular to documents EP0443741, WO2019161360, US2015089751A1 and to US2017208920A1, U.S. Pat. Nos. 5,478,238A and 9,519,927 for foundations, etc.

It should also be noted that the learning models of the various machines forming part of an operational group may be centralized and compared in order to detect deviations and anticipate potential maintenance operations. It is thus possible to detect, for example, a blocked nozzle or conveying tube, or even that a product in a main reservoir has nearly run out and to thus indicate future replacement.

The invention claimed is:

1. A device for dispensing a determined weight of a cosmetic product into a receptacle from a reservoir, the device comprising:
   at least one electromechanical dispensing member capable of moving an amount of cosmetic product from said reservoir installed in the device to a dispensing zone of said device where said amount of product may be transferred through a nozzle into the interior of the receptacle received in said dispensing zone; and
   a controller configured to deliver a control signal to the electromechanical dispensing member according to an error with respect to a setpoint corresponding to the determined weight of cosmetic product to be delivered, said error being determined on the basis of a weighing datum obtained by at least one weighing cell for the reservoir installed in the dispensing zone, wherein the controller is a reinforcement-learning controller.

2. The device according to claim 1, wherein the reinforcement-learning controller uses a regression algorithm according to a Gaussian process.

3. The device according to claim 1, wherein the reinforcement-learning controller uses a deep-reinforcement-learning algorithm.

4. The device according to claim 1, wherein the reinforcement-learning controller is based on an initial predictive model.

5. The device according to claim 1, wherein the reinforcement-learning controller operates without an initial predictive model.

6. The device according to claim 1, wherein the reinforcement-learning controller has been pre-trained prior to commercial use of the device.

7. The device according to claim 1, wherein the reinforcement-learning controller has not been pre-trained prior to commercial use of the device.

8. The device according to claim 1, wherein the reinforcement-learning controller is configured to perform an adaptation of control strategy following a plurality of dispensing operations, in particular after a determined number of dispensing operations and/or after a given period of time, on the basis of the operations performed during this period of time, together defining a dispensing profile.

9. The device according to claim 1, wherein the reinforcement-learning controller is configured to perform one or more adaptations of control strategy over a dispensing operation, in particular at regular intervals after a unitary control action.

10. The device according to claim 1, wherein the electromechanical dispensing member is a positive-displacement pump.

11. The device according to claim 1, wherein the electromechanical dispensing member is a syringe.

12. The device according to claim 1, wherein the device is configured to receive a plurality of reservoirs that are configured for functionally different cosmetic ingredients, said functionally different cosmetic products being capable of being combined so as to form a cosmetic product.

13. The device according to claim 1, wherein the reinforcement-learning controller implements a policy function that defines an action to be performed by the electromechanical dispensing member according to a state of the device during an operation of dispensing a cosmetic product, the state of the device comprising the weighing datum representing the weight of the cosmetic product dispensed into the receptacle and the error with respect to the setpoint.

14. A method for controlling an electromechanical dispensing member with which a device according to claim 1 is equipped, the method comprising:
   providing a setpoint representing a determined weight of product to be dispensed,
   sending a control signal to the electromechanical dispensing member,
   obtaining, from the weighing cell, the weight of product dispensed following the execution of the control command by the electromechanical dispensing member,
   determining a difference between the weight of product dispensed following the execution of the control command and the setpoint,
   modifying the control signal by means of a reinforcement-learning process with a view to minimizing the difference.

15

15. The method according to claim 14 for controlling a device, wherein the control signal corresponds to a complete dispensing profile of the setpoint and is modified after at least one complete dispensing operation.

16. The method according to claim 14 for controlling a device, wherein the control signal corresponds to a unitary incomplete dispensing action, the control signal being modified at least once over the complete dispensing process, the steps of sending the control signal to the electromechanical dispensing member, of obtaining and of determining the difference in dispensing and of adapting the control signal being repeated for as long as said obtained difference is greater than zero.

\* \* \* \* \*

16